US010357663B2

(12) United States Patent
Colbaugh et al.

(10) Patent No.: US 10,357,663 B2
(45) Date of Patent: Jul. 23, 2019

(54) SYSTEM AND METHOD FOR DELIVERING ELECTROMAGNETIC RADIATION TO THE EYEBALL OF A SUBJECT

(75) Inventors: Michael Edward Colbaugh, Level Green, PA (US); Timothy A. Nathan, Pittsburgh, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 780 days.

(21) Appl. No.: 13/265,591

(22) PCT Filed: Mar. 15, 2010

(86) PCT No.: PCT/IB2010/051117
§ 371 (c)(1),
(2), (4) Date: Oct. 21, 2011

(87) PCT Pub. No.: WO2010/122434
PCT Pub. Date: Oct. 28, 2010

(65) Prior Publication Data
US 2012/0041520 A1 Feb. 16, 2012

Related U.S. Application Data

(60) Provisional application No. 61/172,391, filed on Apr. 24, 2009.

(51) Int. Cl.
*A61N 5/06* (2006.01)
(52) U.S. Cl.
CPC .... *A61N 5/0618* (2013.01); *A61N 2005/0648* (2013.01); *A61N 2005/0651* (2013.01);
(Continued)
(58) Field of Classification Search
CPC ............ A61F 9/008; A61F 2009/00872; A61F 9/00821; A61N 2005/0652; A61N 5/0601;
(Continued)

(56) References Cited

U.S. PATENT DOCUMENTS 4,858,609 A * 8/1989 Cole ...................... A61M 21/00
600/26
5,109,852 A * 5/1992 Kaye ........................ A61B 3/16
600/398
(Continued)

FOREIGN PATENT DOCUMENTS

CN 1678675 A 10/2005
EP 1074275 A1 7/2001
(Continued)

OTHER PUBLICATIONS

Definition of Convert. The Free Dictionary, retrieved on Dec. 13, 2016; Retrieved from the Internet: <http://www.thefreedictionary.com/convert>.*
(Continued)

*Primary Examiner* — Gary Jackson
*Assistant Examiner* — Sebastian X Lukjan

(57) ABSTRACT

Light therapy is provided to a subject using a system and/or method. The light therapy includes the administration of electromagnetic radiation to the eyeball of the subject underneath the eyelid of the subject while the eyelid of the subject is closed (e.g., as the subject sleeps). The light therapy algorithm may be designed to impact melatonin and/or serotonin levels within the body of the subject in a therapeutically beneficial manner. For example, the light therapy algorithm may be designed to impact melatonin and/or serotonin levels to treat one or more of a sleep and/or mood disorder (e.g., seasonal affective disorder, non-seasonal depression, Circadian rhythm disruption), or other disorders treatable with control over melatonin and/or serotonin levels in the body.

10 Claims, 7 Drawing Sheets

(52) U.S. Cl.
CPC .............. *A61N 2005/0653* (2013.01); *A61N 2005/0662* (2013.01)

(58) Field of Classification Search
CPC ............ A61N 2005/067; A61N 5/0616; A61N 2005/0644; A61N 5/0614; A61N 2005/0632; A61N 5/06; A61N 1/403; A61N 1/40; A61N 5/0618
USPC ........................... 606/4; 607/88, 89, 91, 100
See application file for complete search history.

(56) References Cited

U.S. PATENT DOCUMENTS

| | | | | |
|---|---|---|---|---|
| 5,507,716 | A * | 4/1996 | LaBerge | A61M 21/00 600/27 |
| 6,155,261 | A * | 12/2000 | Day | 128/846 |
| 6,193,656 | B1 * | 2/2001 | Jeffries | A61B 3/16 600/398 |
| 6,811,257 | B1 | 11/2004 | Lehat | |
| 2001/0056293 | A1 | 12/2001 | Brainard | |
| 2002/0049374 | A1 | 4/2002 | Abreu | |
| 2005/0256273 | A1 | 11/2005 | Imai | |
| 2006/0009822 | A1 * | 1/2006 | Savage | A61M 21/00 607/88 |
| 2006/0173511 | A1 * | 8/2006 | Greenberg et al. | 607/54 |
| 2007/0016074 | A1 * | 1/2007 | Abreu | 600/475 |
| 2008/0081999 | A1 * | 4/2008 | Gravely | A61B 3/10 600/473 |
| 2008/0114423 | A1 * | 5/2008 | Grenon et al. | 607/96 |
| 2008/0170476 | A1 * | 7/2008 | Hurst | 368/250 |
| 2008/0262575 | A1 * | 10/2008 | Aunio et al. | 607/88 |
| 2008/0275533 | A1 * | 11/2008 | Powell | A61N 5/0616 607/88 |
| 2009/0137988 | A1 * | 5/2009 | Kurtz | 606/4 |
| 2009/0203952 | A1 * | 8/2009 | Finger | A61N 5/1001 600/1 |
| 2009/0204186 | A1 * | 8/2009 | Gruber | 607/88 |
| 2009/0216070 | A1 * | 8/2009 | Hunt et al. | 600/27 |
| 2011/0125076 | A1 * | 5/2011 | Kraft | A61F 9/0017 604/20 |
| 2011/0257712 | A1 | 10/2011 | Wells et al. | |
| 2011/0295348 | A1 * | 12/2011 | Paul et al. | 607/90 |
| 2014/0105362 | A1 | 4/2014 | Gertner | |

FOREIGN PATENT DOCUMENTS

| | | |
|---|---|---|
| JP | 08154897 A | 6/1996 |
| JP | 2002528212 A | 9/2002 |
| WO | 2006/109969 A1 | 10/2006 |
| WO | 2008118198 A2 | 10/2008 |
| WO | WO-2008131454 A1 * | 10/2008 |
| WO | 2008/150331 A1 | 12/2008 |

OTHER PUBLICATIONS

Figueiro et al, Preliminary evidence that light through the eyelids can suppress melatonin and phase shift dim light melatonin onset BMC res notes vol. 5, No. 5 p. 221.*

Hatonen et al. Suppression of melatonin by 2000-lux light in humans with closed eyelids. Biological Psychiatry, vol. 46 Issue 6, Sep. 15, 1999, pp. 827-831 [online], [retrieved on Feb. 14, 2018]. Retrieved from the Internet <URL:https://www.sciencedirect.com/science/article/pii/S0006322398003576>.*

Cajochen et al. Dose-response relationship for light intensity and ocular and electroencephalographic correlates of human alertness. Behavioural Brain Research, 115 (2000) pp. 75-84 [retrieved on Feb. 14, 2018]. Retrieved from the Internet <URL: https://www.sciencedirect.com/science/article/pii/S0166432800002369?via%3Dihub>.*

"Contact Lenses for Superhuman Vision", UW College of Engineering, htt;://www.engr.washington.edu/facresearch/highlights/eecontactlens.html, Downloaded Jul. 22, 2014, pp. 1-2.

"Low Blue Lights", https?www.lowbluelights.com/index.asp?, Downloaeded Jul. 22, 2014, pp. 1-5.

* cited by examiner

Cross section A-A

View A-A

Cross section A-A

View A-A

Eyelids closed

Cross section A-A

Eyelids closed

Cross section A-A

View A-A

Cross section A-A

View A-A

SYSTEM AND METHOD FOR DELIVERING ELECTROMAGNETIC RADIATION TO THE EYEBALL OF A SUBJECT

This application claims benefit under 35 U.S.C. § 119(e) of U.S. Provisional Application No. 61/172,391 filed on Apr. 24, 2009, the contents of which are herein incorporated by reference.

The invention relates to a medical system and/or method for implementing the delivery of electromagnetic radiation to the eyeball of a sleeping subject in accordance with a light therapy algorithm designed to impact melatonin and/or serotonin levels within the subject.

Systems designed to deliver electromagnetic radiation to the eye of a sleeping subject to provide light therapy to the subject are known. These systems generally require electromagnetic radiation within a predetermined wavelength range that is therapeutically effective to be directed onto the eyelid of the subject. The eyelid of the subject will block and/or absorb much of the electromagnetic radiation within the predetermined wavelength. So conventional systems generally provide electromagnetic radiation within the predetermined wavelength onto the eye of the subject at a relatively high intensity.

One aspect of the invention relates to a system configured to provide light therapy to a subject. In one embodiment, the system comprises a radiation introduction module and a processor. The radiation introduction module is configured to rest at least partially disposed between an eyeball and an eyelid of a subject during use, and to deliver electromagnetic radiation to the eyeball of the subject under the eyelid of the subject while the subject is asleep to provide light therapy to the subject. The processor is configured to control the introduction of the electromagnetic radiation to the eyeball of the subject to impact melatonin and/or serotonin levels in a therapeutically beneficial manner.

Another aspect of the invention relates to a method of providing light therapy to a subject. In one embodiment, the method comprises delivering electromagnetic radiation to an eyeball of a subject under an eyelid of the subject while the subject is asleep to impact melatonin and/or serotonin levels in a therapeutically beneficial manner.

Yet another aspect of the invention relates to a system configured to provide light therapy to a subject. In one embodiment, the system comprises means for delivering electromagnetic radiation to an eyeball of a subject under an eyelid of the subject while the subject is asleep to impact melatonin and/or serotonin levels in a therapeutically beneficial manner.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
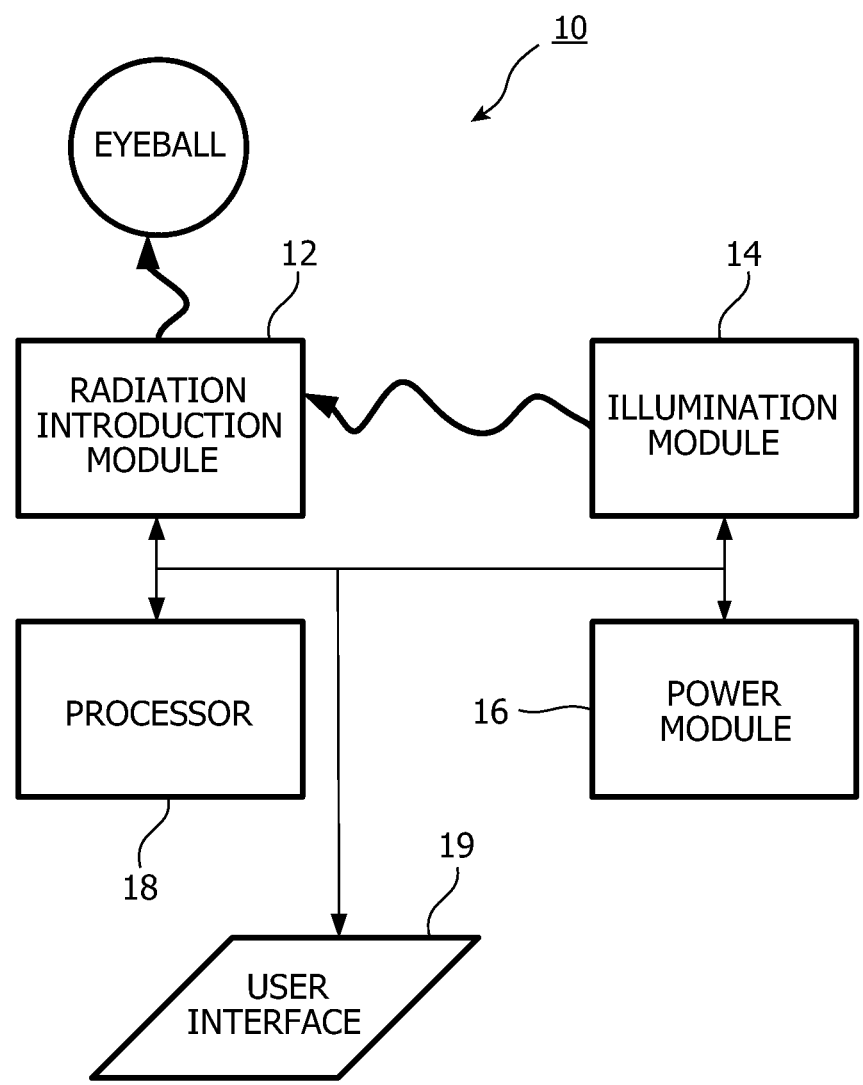
FIG. 1 illustrates a system configured to provide light therapy to a subject, according to one or more embodiments of the invention.

FIG. 1 illustrates a system 10 configured to provide light therapy to a subject. The light therapy includes the administration of electromagnetic radiation to the eyeball of the subject underneath the eyelid of the subject while the eyelid of the subject is closed (e.g., as the subject sleeps). The therapy may include delivering electromagnetic radiation to the subject while the eye of the subject is open from a member that rests directly on the eyeball of the subject. The electromagnetic radiation is delivered to the eyeball of the subject with one or more parameters (e.g., wavelength, timing, duration, one or more pulse parameters, etc.) that are dictated by a light therapy algorithm. The light therapy algorithm may be designed to impact melatonin and/or serotonin levels within the body of the subject in a therapeutically beneficial manner. For example, the light therapy algorithm may be designed to impact melatonin and/or serotonin levels to treat one or more of a sleep and/or mood disorder (e.g., seasonal affective disorder, non-seasonal depression, Circadian rhythm disruption), or other disorders treatable with control over melatonin and/or serotonin levels in the body. In one embodiment, system 10 includes one or more of a radiation introduction module 12, an illumination module 14, a power module 16, a processor 18, a user interface module 19, and/or other components.

In one embodiment, radiation introduction module 12 is configured to rest at least partially between the eyeball and the eyelid of the subject during use, and deliver radiation to the eyeball of the subject underneath the eyelid of the subject. For example, as is discussed further below, radiation introduction module 12 may include a body portion forming an electromagnetic radiation delivery surface that rests on an outer surface of the eyeball. For example, the body portion may be formed similar to a conventional contact lens that conforms to an outer surface of the eyeball to rest thereon. This is not intended to be limiting. For instance, radiation introduction module 12 may include a tattoo or other permanent or semi-permanent substance or device disposed under the eyelid of the subject and configured to deliver electromagnetic radiation to the surface of the eyeball of the subject.

To introduce electromagnetic radiation to the eyeball of the subject, radiation introduction module 12 may be formed, at least in part, from one or more transparent and/or translucent materials configured to direct illumination onto the eyeball of the subject. The materials used to form radiation introduction module 12 may have properties (e.g., refractive properties, diffusive properties, reflective properties, etc.) designed to guide the electromagnetic radiation to the eyeball of the subject.

As is discussed further below, in one embodiment radiation introduction module 12 includes a guide portion as well as a body portion. The guide portion may be formed on a side of the body portion opposite the electromagnetic radiation delivery surface. The guide portion is configured to sit between the upper eyelid and the lower eyelid of the subject, and to guide electromagnetic radiation from the exterior of the eyelid to the body portion of radiation introduction module 12 for delivery to the eyeball of the subject.

As was mentioned above, the light therapy algorithm used to control the administration of electromagnetic radiation to the subject may dictate a wavelength of the electromagnetic radiation. For example, the light therapy algorithm may dictate that the electromagnetic radiation directed to the eyeball of the subject have a wavelength within a predetermined wavelength range. The wavelength range may include a range of wavelengths at which electromagnetic radiation is therapeutically beneficial in controlling levels of melatonin and/or serotonin within the body. For instance, the predetermined wavelength range may include wavelengths between about 410 nm and about 580 nm.

Radiation introduction module 12 may be configured to process electromagnetic radiation between the eyeball and the eyelid of the subject to convert wavelengths of the electromagnetic radiation to within the predetermined range. This may enhance the amount of therapeutically beneficial electromagnetic radiation provided to the eyeball of the subject through the eyelid because electromagnetic radiation having wavelengths longer than the predetermined wavelength range may penetrate the eyelid with greater transmittance than electromagnetic radiation with wavelengths in the predetermined wavelength range.

By way of non-limiting example, electromagnetic radiation at relatively large wavelengths in the visible or near-visible spectrum (e.g., yellow, orange, red, infrared, etc.) passes through the eyelid at a greater transmittance than electromagnetic radiation in the predetermined wavelength range. Radiation introduction module 12 may convert the wavelength of such radiation to within the predetermined wavelength range through frequency doubling. Transmitting and processing electromagnetic radiation in this manner may be more efficient than simply transmitting electromagnetic radiation within the predetermined wavelength through the eyelid of the subject.

The illumination module 14 may be configured to provide electromagnetic radiation to the eye of the subject that will be converted by radiation introduction module 12 to electromagnetic radiation within the predetermined wavelength. The provision of such electromagnetic radiation by illumination module 14 may be controlled by processor 18 such that the electromagnetic radiation converted by radiation introduction module 12 is provided to the eyeball of the subject in accordance with the light therapy algorithm.

In one embodiment, radiation introduction module 12 may be configured to selectively block some electromagnetic radiation from reaching the eyeball of the subject when the eyelid is open. For example, radiation introduction module 12 may include a lens that selectively filters out electromagnetic radiation at within a predetermined wavelength range. Wavelengths within the predetermined wavelength range may include wavelengths that impact melatonin and/or serotonin levels within the body. For instance, the predetermined wavelength range may include wavelengths between about 410 nm and about 580 nm. For example, a color gel filter material may be used to coat the outer surface of radiation introduction module 12 (e.g., a surface facing away from the eyeball). As another example, the radiation introduction module 12 may be designed to be Schott glass colored optical filter.

The illumination module 14 may be configured to provide the electromagnetic radiation that is delivered to the eyeball of the subject by radiation introduction module 12. As such, illumination module 14 may include one or more radiation sources configured to emit the electromagnetic radiation. The one or more radiation sources may include a Light Emitting Diode ("LED"), an Organic Light Emitting Diode ("OLED"), an electroluminescent radiation source ("EL source"), a photoluminescent radiation source ("PL source"), an incandescent source, a laser source, and/or other radiation sources.

As is discussed further below, the one or more radiation sources may include one or more radiation sources carried by radiation introduction module 12 between the eyelid and the eyeball of the subject, one or more radiation sources disposed on the exterior of the eyelid of the subject, a combination radiation sources under the eyelid and on the exterior of the eyelid. The one or more radiation sources may include a radiation source configured to emit electromagnetic radiation at a therapeutically beneficial wavelength (e.g., within the predetermined wavelength range). The one or more radiation sources may include a radiation source configured to emit electromagnetic radiation at a wavelength that can be converted to a therapeutically beneficial wavelength by radiation introduction module 12.

In one embodiment, illumination module 14 is configured to deliver ambient electromagnetic radiation to radiation introduction module 12. In this embodiment, illumination module 14 may or may not include other radiation sources that generate electromagnetic radiation.

In one embodiment, radiation introduction module 12 may be configured to store energy, and to release energy gradually over time in the form of electromagnetic radiation. The electromagnetic radiation may have a therapeutically effective wavelength. By way of non-limiting example, radiation introduction module 12 may include a long-decay rechargeable phosphor material that can be charged, and then emits electromagnetic radiation gradually over time. In such an embodiment, illumination module 14 may be configured to deliver electromagnetic radiation to radiation introduction module 12 during periods of time when system is not installed on the eyeball of the subject. The electromagnetic radiation delivered by illumination module 14 may include electromagnetic radiation having a wavelength that is effective to charge the long-decay rechargeable phosphor material.

The power module 16 is configured to deliver power to some or all of the radiation sources in illumination module 14 to enable the one or more radiation sources to generate electromagnetic radiation. Power module 16 may deliver power to the radiation sources via a wired connection and/or via a wireless connection. In embodiments in which power module 16 delivers power to the one or more radiation sources of illumination module 14 wirelessly, power module 16 includes a power transmission module and a power reception module. The power transmission module generates the wireless power transmission. The power reception module receives the wireless power transmission, and delivers the received power to the one or more radiation sources. Power module 16 may deliver the power to the one or more radiation sources from one or more energy supplies. The one or more energy supplies may include, for example, a battery, a wall socket, and/or other energy supplies.

Processor 18 is configured to provide control capabilities in system 10. As such, processor 18 may include one or more of a digital processor, an analog processor, a digital circuit designed to process information, an analog circuit designed to process information, a state machine, and/or other mechanisms for providing control of electronic components. Although processor 18 is shown in FIG. 1 as a single entity, this is for illustrative purposes only. In some implementations, processor 18 may include a plurality of processing units. These processing units may be physically located within the same device, or processor 18 may represent processing functionality of a plurality of devices operating in coordination. For example, in one embodiment, the functionality attributed below to processor 18 is divided between a first processor disposed in a device located outside of the eyeball of the subject (e.g., in a sleep mask or bedside unit), and a second processor disposed in a device that rests, at least in part, between the eyelid and the eyeball of the subject (e.g., in radiation introduction module 12).

Processor 18 controls illumination module 14 and/or power module 16 to provide electromagnetic radiation to radiation introduction module 12 for delivery to the eyeball of the subject in accordance with a light therapy algorithm. The light therapy algorithm may dictate one or more parameters of the electromagnetic radiation delivered to the eyeball of the subject to control the level of melatonin and/or serotonin within the subject. The one or more parameters of the electromagnetic radiation may include one or more of an intensity, a wavelength, a flux, a timing, a duration, a pulse frequency, a pulse width, an illumination direction, an illumination pattern, a subtended angle of illumination, and/or other parameters.

By way of non-limiting example, the light therapy algorithm may be designed to impact the Circadian rhythms of the subject. For instance, in one embodiment, the light therapy is designed to treat Phase Delay Syndrome in the subject. "Night-owl" teenagers commonly suffer from a late-night shifted sleeping schedule associated with Phase Delay Syndrome. To treat Phase Delay Syndrome, the light therapy algorithm implemented by processor 18 dictates that efficacious levels of electromagnetic radiation should be delivered to the subject after the subject's circadian phase-zero towards the morning. This administration of electromagnetic radiation via system 10 may be coupled with restricted light exposure and exogenous melatonin administration prior to bed time. Such treatment is known as Phase Advance treatment.

In controlling system 10 to deliver the electromagnetic radiation to the subject underneath the eyelid of the subject in accordance with the light therapy algorithm designed to treat Phase Delay Syndrome, processor 18 may control radiation introduction module 12 and/or illumination module to deliver electromagnetic radiation to the eyeball of the subject while the subject is in bed and/or sleeping. This may include commencing the direction of therapeutically effective electromagnetic radiation to the eyeball at a predetermined time of night, at some predetermined time after bedtime (e.g., bedtime may be inferred from a time of installation of radiation introduction module 12 on the eye of the subject), at some predetermined time after sleep commences, and/or other predetermined times).

In one embodiment, processor 18 controls the intensity of the electromagnetic radiation such that the illuminance of the radiation is ramped up from an initial level (e.g., at or near zero lux) to an efficacious level (e.g., between about 0.000001 lux and about 50 lux, between about 0.0001 lux and about 30 lux, etc.). The ramping may be performed in accordance with a sigmoid intensity progression (e.g., to simulate dawn), or some other pattern. The electromagnetic radiation may be pulsed in accordance with a predetermined frequency, pulse width, and/or other pulse parameters. The processor 18 may continue to control system 10 to provide electromagnetic radiation at the therapeutic wavelength and/or illuminance to the eyeball of the subject for a predetermined period of time, or until a reset is received manually from the subject.

In one embodiment, processor 18 controls system 10 to deliver electromagnetic radiation to the eyeball of the subject that is not therapeutically effective (e.g., in the red/orange range of the visible spectrum) before the subject goes to sleep. This may enable the subject to become accustomed to the introduction of radiation to the eyeball while still awake, thereby decreasing the chances that the therapeutic radiation will waken the subject. In this embodiment, as the illuminance/intensity of the therapeutically beneficial radiation is ramped up, the illuminance/intensity of the initial radiation may be reduced such that the overall illuminance of the radiation provided to the eyeball of the subject remains substantially unchanged.

In one embodiment, the control over system 10 by processor 18 to provide therapeutically beneficial electromagnetic radiation to the is dynamic based on one or more parameters monitored by sensors included in system 10 (not shown in FIG. 1). These sensors may monitor, for example, a sleep state of the subject, whether the eyelid of the subject is open or closed, wakefulness of the subject, an intensity or illuminance of the therapeutically beneficial electromagnetic radiation, the wavelength of the electromagnetic radiation directed to the eyeball, and/or other parameters. Control of system 10 by processor 18 based on sensors monitoring in this manner may reduce disturbance of the sleep of the subject, enhance the uniformity of the electromagnetic radiation delivered to the eyeball of the subject, and/or provide other enhancements.

It should be appreciated that because the therapeutically effective electromagnetic radiation is provided to the eyeball by system 10 without requiring the electromagnetic radiation to pass through the eyelid, the amount of radiation that must be generated by system 10 in accordance with the light therapy algorithm is significantly lower than conventional system in which the therapeutically effective electromagnetic radiation is transmitted through the eyelid.

User interface 19 is configured to provide an interface between system 10 and the subject through which the subject, or some other user (e.g., a caregiver) may provide information to and receive information from system 10. This enables data, results, and/or instructions and any other communicable items, collectively referred to as "information," to be communicated between the subject the system 10. For instance, one or more of the parameters of the light therapy algorithm may be set and/or overridden by a user via user interface 19. Similarly, a user may initiate and/or reset the light therapy algorithm via user interface 19. Examples of interface devices suitable for inclusion in user interface 19 include a keypad, buttons, switches, a keyboard, knobs, levers, a display screen, a touch screen, speakers, a microphone, an indicator light, an audible alarm, and a printer.

It is to be understood that other communication techniques, either hard-wired or wireless, are also contemplated by the present invention as user interface 19. For example, the present invention contemplates that user interface 19 may include a removable storage device that can be interfaced with system 10 provide information to system 10 and/or receive information from system 10. Other exemplary input devices and techniques adapted for use with system 10 as user interface 19 include, but are not limited to, an RS-232 port, RF link, an IR link, modem (telephone, cable or other). In short, any technique for communicating information with system 10 is contemplated by the present invention as user interface 19.

Figure 2:
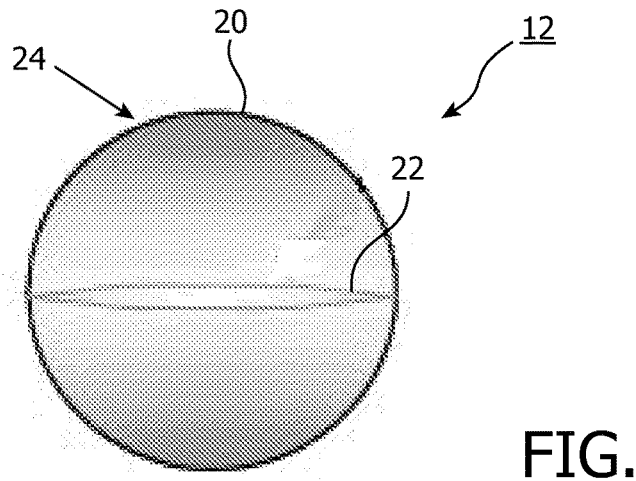
FIG. 2 illustrates a radiation introduction module, in accordance with one or more embodiments of the invention.
Figure 3:
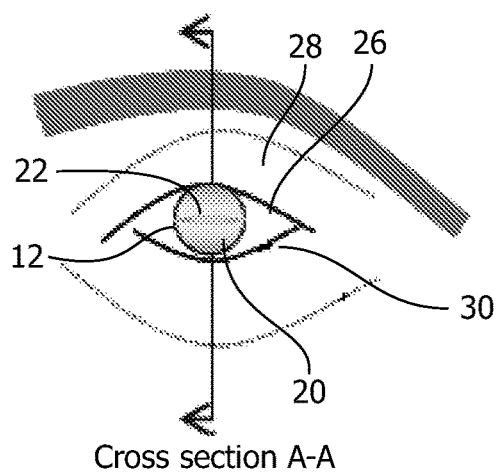
FIG. 3 illustrates a radiation introduction module, in accordance with one or more embodiments of the invention.
Figure 4:
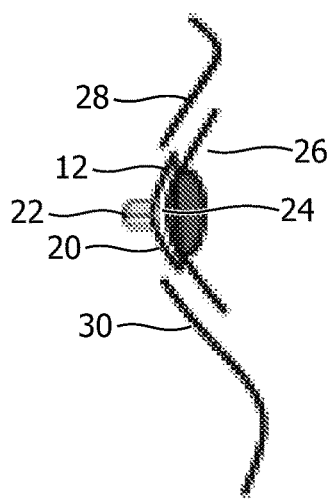
FIG. 4 illustrates a radiation introduction module, in accordance with one or more embodiments of the invention.

FIGS. 2-4 illustrate one embodiment of radiation introduction module 12. As can be seen in FIGS. 2-4, radiation introduction module 12 includes a body portion 20 and a guide portion 22. Body portion 20 forms an electromagnetic radiation delivery surface 24. The electromagnetic radiation delivery surface 24 is formed on body portion 20 on a side of body portion 20 that faces into the page in FIGS. 2 and 3. The electromagnetic radiation delivery surface 24 is configured to engage the surface of the eyeball 26 of the subject.

On a side of body portion 20 opposite from electromagnetic radiation delivery surface 24, guide portion 22 is formed. The guide portion 22 protrudes outwardly from body portion 20. In one embodiment, guide portion 22 is formed as a ridge that runs along body portion 20. As can be seen in FIG. 4, if the subject closes the upper eyelid 28 and the lower eyelid 30, guide portion 22 sits between upper eyelid 28 and lower eyelid 30. While guide portion 22 protrudes through upper eyelid 28 and lower eyelid 30, guide portion 22 also cooperates with upper eyelid 28 and lower eyelid 30 to seal the eye (e.g., to prevent drying and irritation).

The guide portion 22 and body portion 20 are formed from one or more transparent and/or translucent materials so that electromagnetic radiation can pass through guide portion 22 and body portion 20. The guide portion 22 and body portion 20 are configured to direct electromagnetic radiation from outside of eyelids 28 and 30, through guide portion 22 into body portion 20 and onto eyeball 26 through electromagnetic radiation delivery surface 24.

In one embodiment, radiation introduction module 12 as illustrated in FIGS. 2-4 is implemented with a device that provides electromagnetic radiation to guide portion 22 as the subject sleeps in accordance with a light therapy algorithm. For instance, the device may provide the functionality attributed to illumination module 14, power module 16, and/or processor 18 described above with respect to FIG. 1.

By way of non-limiting example, the device may include a sleep mask with one or more radiation sources integrated therein that emit electromagnetic radiation directed to guide portion 22. Non-limiting examples of such a sleep mask are provided in U.S. Provisional Patent Application No. 61/141,289, filed Dec. 30, 2008, and entitled "SYSTEM AND METHOD FOR PROVIDING LIGHT THERAPY TO A SUBJECT". These applications are hereby incorporated by reference into the present disclosure in their entirety.

Figure 5:
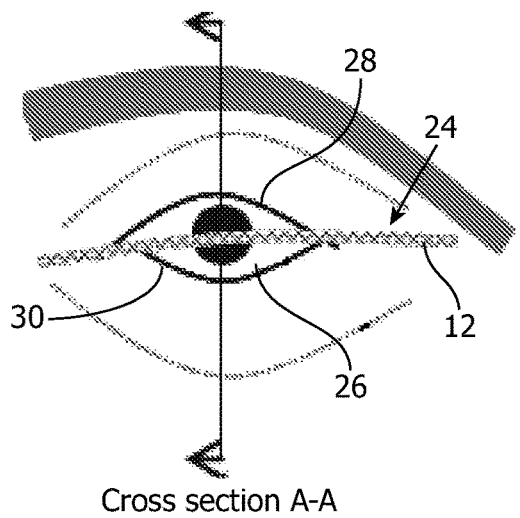
FIG. 5 illustrates a radiation introduction module, in accordance with one or more embodiments of the invention.
Figure 6:
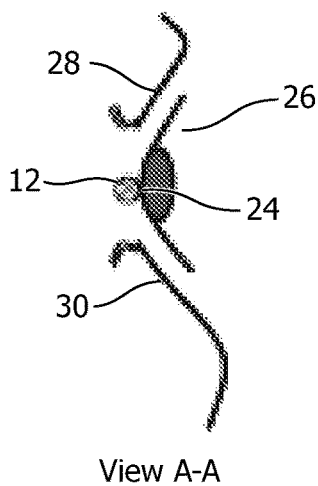
FIG. 6 illustrates a radiation introduction module, in accordance with one or more embodiments of the invention.
Figure 7:
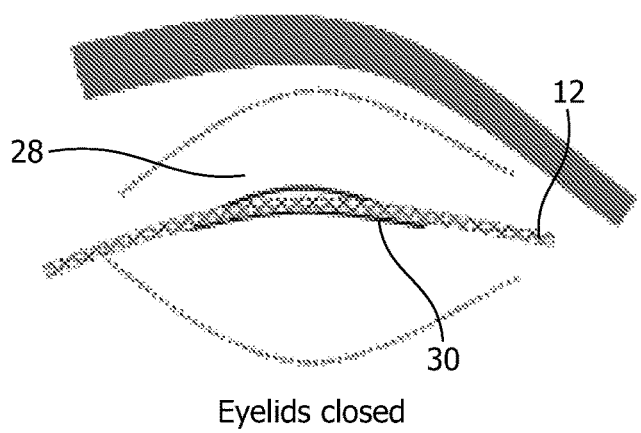
FIG. 7 illustrates a radiation introduction module, in accordance with one or more embodiments of the invention.
Figure 8:
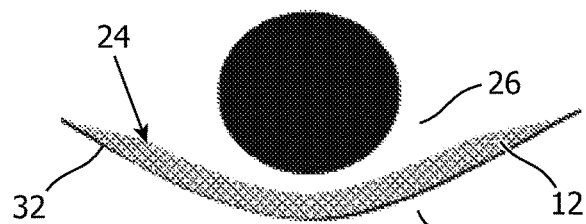
FIG. 8 illustrates a radiation introduction module, in accordance with one or more embodiments of the invention.
Figure 9:
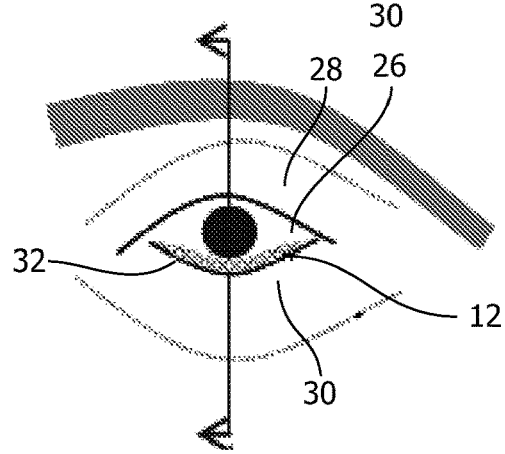
FIG. 9 illustrates a radiation introduction module, in accordance with one or more embodiments of the invention.
Figure 10:
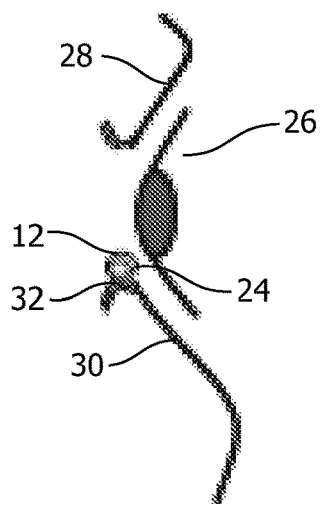
FIG. 10 illustrates a radiation introduction module, in accordance with one or more embodiments of the invention.
Figure 11:
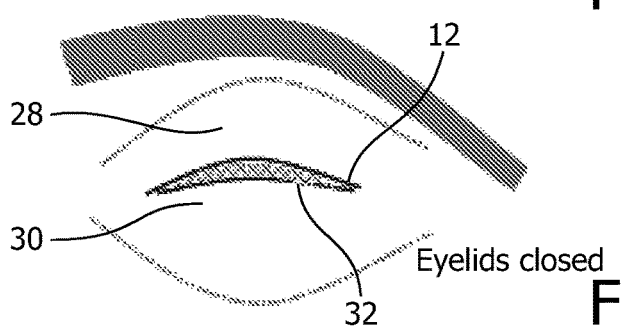
FIG. 11 illustrates a radiation introduction module, in accordance with one or more embodiments of the invention.

FIGS. 5-7 illustrate one embodiment of radiation introduction module 12. In the embodiment of radiation introduction module 12 illustrated in FIGS. 5-7, the body portion and the guide portion of radiation introduction module 12 are formed as a single light guide member that provides a relatively thin electromagnetic radiation delivery surface 24. For example, radiation introduction module 12 may be formed from a fiber light guide that rests on eyeball 26 and sits between upper eyelid 28 and lower eyelid 30 when the eye is closed. The embodiment of radiation introduction module 12 operates in substantially the same manner as the embodiment of radiation introduction module 12 discussed above with respect to FIGS. 2-4 to direct light from the exterior of upper eyelid 28 and lower eyelid 30 onto eyeball 26 through electromagnetic radiation delivery surface 24. The embodiment of radiation introduction module 12 illustrated in FIGS. 5-7 may be implemented with a device configured to provide electromagnetic radiation to radiation introduction module 12 as the subject sleeps, as was discussed above.

FIGS. 8-11 illustrate an embodiment of radiation introduction module 12. In the embodiment of radiation introduction module 12 illustrated in FIGS. 8-11, radiation introduction module 12 includes an adhesive surface 32. The member page module 32 is configured to releasably adhere to one of upper eyelid 28 or lower eyelid 30. By virtue of this adhesion, if the subject opens the eye, radiation introduction module 12 will be moved out of (or at least toward the edge of) the field of vision of the subject by the opening of upper eyelid 28 and lower eyelid 30. The embodiment of radiation introduction module 12 illustrated in FIGS. 5-7 may be implemented with a device configured to provide electromagnetic radiation to radiation introduction module 12 as the subject sleeps, as was discussed above with respect to the embodiment of radiation introduction module 12 illustrated in FIGS. 2-4.

Figure 12:
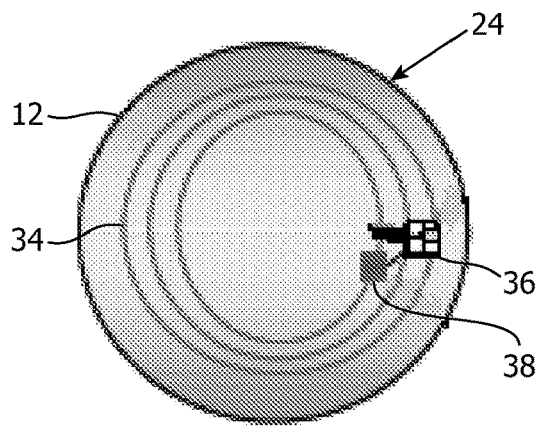
FIG. 12 illustrates a radiation introduction module, in accordance with one or more embodiments of the invention.
Figure 13:
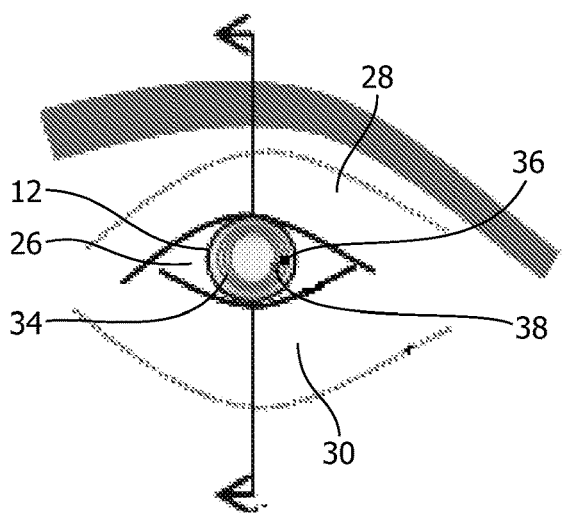
FIG. 13 illustrates a radiation introduction module, in accordance with one or more embodiments of the invention.
Figure 14:
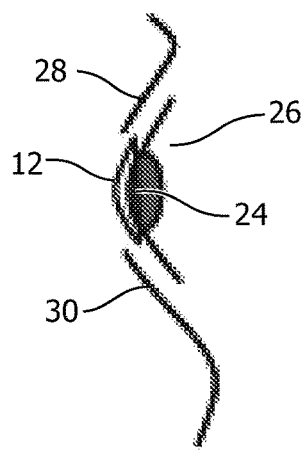
FIG. 14 illustrates a radiation introduction module, in accordance with one or more embodiments of the invention.

FIGS. 12-14 illustrate an embodiment of radiation introduction module 12. In particular, the embodiment of radiation introduction module 12 illustrated in FIGS. 12-14 is formed as a lens or body that fits between eyeball 26 and eyelids 28 and 30. Electromagnetic radiation is delivered to eyeball 26 through electromagnetic radiation delivery surface 24 formed by radiation introduction module 12.

The embodiment of radiation introduction module 12 shown in FIGS. 12-14 further includes at least a portion of illumination module 14 and power module 16. More particularly, radiation introduction module 12 includes an antenna 34, electronic circuitry 36, and radiation source 38 carried by body portion 20.

The antenna 34 and electronic circuitry 36 are configured to provide at least some of the functionality attributed above to power module 16. Specifically, The antenna 34 is formed as a coil that receives electromagnetic radiation transmitted from a transmitter coupled to an energy supply that forms an inductive coupling between antenna 34 and the transmitter, thereby enabling transmission of power from the energy supply to antenna 34. The electronic circuitry 36 includes one or more electronic circuits configured to condition the power received by antenna 34 to be suitable for use by the other components carried by radiation introduction module 12.

The radiation source 38 may include one or more sources of electromagnetic radiation. Radiation source 38 is electronically coupled to electronic circuitry 36, and is powered antenna 34 and electronic circuitry 36 to emit electromagnetic radiation. The electromagnetic radiation emitted by the radiation source 38 has a therapeutic wavelength, and is delivered to eyeball 26 through radiation introduction module 12.

In one embodiment, electronic circuitry 36 includes not only power conditioning circuitry, but also circuitry that provides some or all of the functionality attributed to processor 18 above. For example, electronic circuitry 36 may include circuitry that controls one or more parameters of the electromagnetic radiation emitted by radiation source 38 in accordance with the light therapy algorithm.

Figure 15:
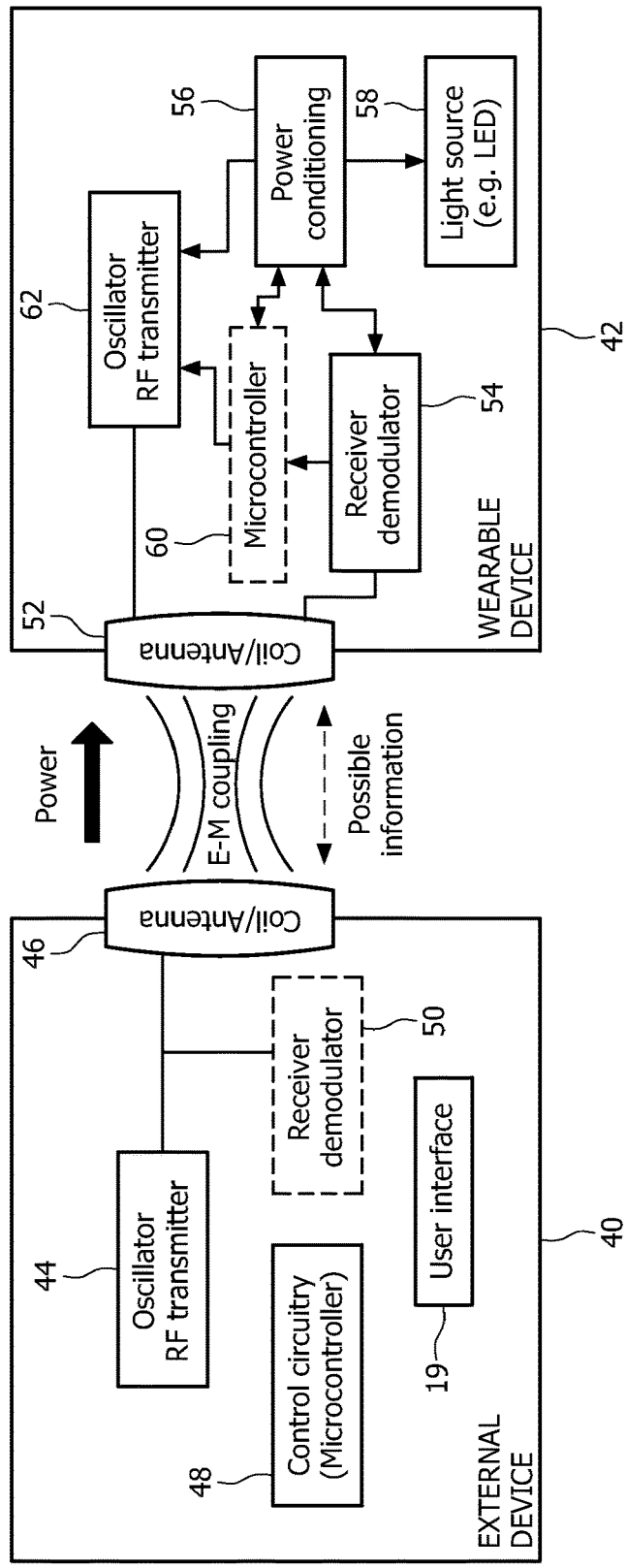
FIG. 15 illustrates a system configured to provide light therapy to a subject, according to one or more embodiments of the invention.

FIG. 15 provides a schematic diagram of system 10 including an embodiment of radiation introduction module 12 that carries at least portions of illumination module 14, power module 16, and/or processor 18 (e.g., as illustrated in FIGS. 12-14 and described above). In the embodiment shown, system 10 includes an external device 40 and a wearable device 42. It will be appreciated that external device 40 may be wearable, however, in the embodiment of system 10 illustrated only wearable device 42 is actually worn in the eye of the subject, while external device 40 is positioned externally from the subject.

The external device 40 is an apparatus that is configured to provide at least some of the functionality of system 10 attributed to one or more of power module 16, processor 18, and/or user interface 19 above in the description of FIG. 1. In the embodiment of external device 40 illustrated in FIG. 15, external device 40 includes one or more of an electromagnetic radiation transmitter 44, an antenna 46, a processor 48, and/or user interface 19.

The electromagnetic radiation transmitter 44 and antenna 46 are configured to transmit power and/or information to wearable device 42 wirelessly. The electromagnetic radiation transmitter 44 and antenna 46 transmit power wirelessly to wearable device 42 by generating a signal of electromagnetic radiation that creates an inductive coupling between antenna 46 and a corresponding antenna on wearable device 42 (e.g., antenna 52 described below). The power to transmit the electromagnetic radiation that creates the inductive coupling, as well as perform the other functions attributed to external device 40, is obtained from one or more energy supplies (e.g., battery, wall socket, etc.). In transmitting power to wearable device 42, electromagnetic radiation transmitter 44 and antennae 46 provide at least some of the functionality attributed to power module 16 (shown in FIG. 1 and described above).

In addition to transmitting power to wearable device 42, electromagnetic radiation transmitter 44 and antennae 46 may transmit communication signals to wearable device 42. The communication signals may provide a mechanism for communication between the components of external device 40 (e.g., processor 48) and wearable device 42.

The processor 48 may provide at least some of the functionality attributed above to processor 18 (shown in FIG. 1 and described above). For example, processor 48 may control electromagnetic radiation transmitter 44 and/or antennae 46 such that the power transmitted to wearable device 42 from external device 40 causes wearable device 42 to emit radiation with one or more parameters that vary in accordance with a light therapy algorithm.

In one embodiment, external device 40 is configured to receive communication transmitted from wearable device 42. In this embodiment, external device 40 includes a receiver 50 operatively coupled with antennae 46. Receiver 50 is configured to receive and/or demodulate communication signals received wirelessly by antennae 46, and to provide the received and demodulated signal to processor 48 for processing. The communication signals received from wearable device 42 may include, for example, information related to the operation of wearable device 42 (e.g. feedback information).

The wearable device 42 is a device configured to be worn on the eye of the subject. Wearable device 42 may provide at least some of the functionality attributed above to radiation introduction module 12, illumination module 14, power module 16, and/or processor 18 (shown in FIG. 1 and described above). The components of wearable device 42 shown in FIG. 15 may be carried by a module that is similar to or the same as the embodiment of radiation introduction module 12 illustrated in FIGS. 1-14 and described above. In one embodiment, wearable device 42 includes one or more of an antenna 52, a receiver 54, a power conditioner 56, a radiation source 58, and/or other components.

Antenna 52, receiver 54, and power conditioner 56 are configured to receive power for components of wearable device 42. In particular, antenna 52 is formed as a coil that is inductively couples with antennae 46 of external device 40 to receive power transmissions from external device 40. Receiver 54 and power conditioner 56 function to condition the power received via antennae 46 for consumption by the components of wearable device 42. For example, the power received by antenna 52, receiver 54, and power conditioner 56 may be used to drive radiation source 58. As such, antenna 52, receiver 54, and power conditioner 56 may provide at least some of the functionality attributed above to power module 16 (shown in FIG. 1 and described above).

The radiation source 58 includes one or more radiation sources that are powered by power from power conditioner 56 to emit electromagnetic radiation. One or more of the parameters of the electromagnetic radiation emitted by radiation source 58 are controlled in accordance with a light therapy algorithm. This control may be provided by components on external device 40 that communicate with wearable device 42 (e.g., between antennae 46 and antenna 52), and/or by components within wearable device 42. The radiation source 58 may provide the functionality attributed above to illumination module 14 (shown in FIG. 1 and described above) and/or radiation source 38 (shown in FIGS. 12 and 13, and described above).

In one embodiment, wearable device 42 includes one or both of a processor 60 and/or a transmitter 62. In this embodiment, processor 60 is configured to control one or more of the other components of wearable device 42. For example, processor 60 may be configured to control one or more of receiver 54, power conditioner 56, and/or radiation source 58 such that the one or more of the parameters of the electromagnetic radiation generated by radiation source 38 are dictated by a light therapy algorithm. In such instances, processor 60 may cooperate with processor 48 in external device 40 to provide the control, or processor 60 may control the components of wearable device 42 without input from processor 48.

The transmitter 62 may be configured to transmit communication information from wearable device 42 to external device 40 via antenna 52. This may enable processor 60 to communicate with one or more components of external device 40. For example, processor 60 may communicate with one or both of processor 48 and/or user interface 19.

Figure 16:
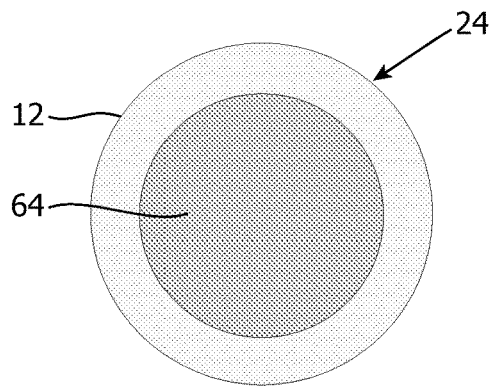
FIG. 16 illustrates a radiation introduction module, in accordance with one or more embodiments of the invention.
Figure 17:
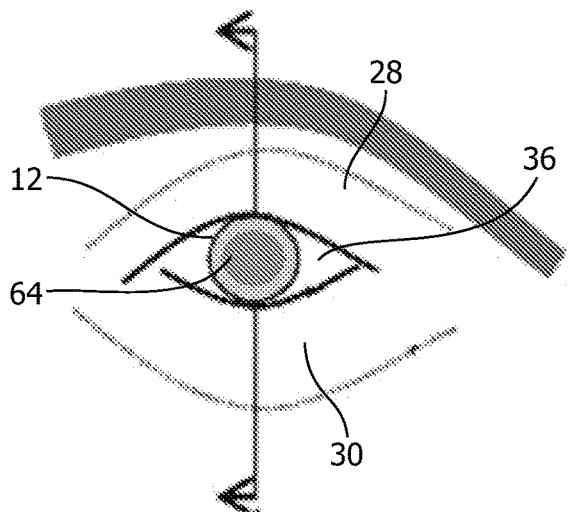
FIG. 17 illustrates a radiation introduction module, in accordance with one or more embodiments of the invention.
Figure 18:
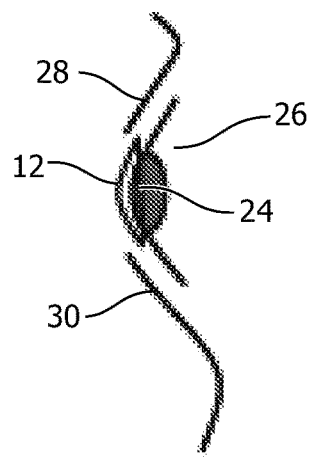
FIG. 18 illustrates a radiation introduction module, in accordance with one or more embodiments of the invention.

FIGS. 16-18 illustrate an embodiment of radiation introduction module 12. In the embodiment illustrated in FIGS. 16-18, radiation introduction module 12 is formed as a lens type of body that rests between eyeball 26 of the subject and eyelids 28 and 30. In or on radiation introduction module 12, a radiation source 64 is disposed. Radiation source 64 provides at least some of the functionality attributed above to illumination module 14 (shown in FIG. 1 and described above). In particular, radiation source 64 is formed from one or more photoluminescent materials. The one or more photoluminescent materials are materials that absorb photons of light, and then re-radiate photons. Some or all of the photons re-radiated by the photoluminescent materials of radiation source 64 are directed to eyeball 26 of the subject through electromagnetic radiation delivery surface 24 of radiation introduction module 12.

In order to be therapeutically beneficial, the photons of electromagnetic energy directed from radiation source 64 to eyeball 26 by radiation introduction module 12 may need to be within a predetermined wavelength range (e.g., 410 nm-580 nm, blue-green, around 480 nm, etc.). The photoluminescent materials within radiation source 64 are configured to absorb photons of light that do not have wavelengths within the predetermined wavelength range, and to emit at least some photons within the predetermined wavelength range.

In one embodiment, the photoluminescent materials within radiation source 64 are configured to absorb electromagnetic radiation at wavelengths that pass through eyelids 28 and 30 with a greater transmittance than electromagnetic radiation within the predetermined wavelength range. For example, electromagnetic radiation at wavelengths larger than the predetermined wavelength range (e.g., yellow, orange, red, infrared, etc.) may pass through the eyelids 28 and 30 at a greater transmittance than electromagnetic radiation in the predetermined wavelength range.

By absorbing electromagnetic radiation that passes through eyelids 28 and 30 with a relatively large transmittance, and then emitting electromagnetic radiation within the predetermined wavelength range, radiation source 64 may enhance the delivery of electromagnetic radiation to eyeball 26 of the subject. For example, implementation of radiation source 64 within radiation introduction module 12 may reduce the intensity of electromagnetic radiation that is directed to the eye of the subject while the subject sleeps in order to provide the appropriate amount of electromagnetic radiation within the predetermined wavelength range.

In one embodiment, the electromagnetic radiation emitted by 64 includes some electromagnetic radiation that does not have a wavelength within the predetermined wavelength range. In this embodiment, radiation introduction module 12 may include one or more filters that selectively block electromagnetic radiation emitted by radiation source 64 with wavelengths outside of the predetermined wavelength range.

It will be appreciated that although radiation source 64 is illustrated in FIGS. 16-18 as a single body formed from photoluminescent materials, this is not intended to be limiting. In one embodiment, radiation source 64 includes a plurality of discrete pockets or bodies of photoluminescent materials formed in and/or on radiation introduction module 12. In one embodiment, radiation source 64 includes photoluminescent materials distributed throughout radiation introduction module 12.

In one embodiment, radiation introduction module 12 as illustrated in FIGS. 16-18 is implemented with a device that provides electromagnetic radiation to eyelids 28 and 30 as the subject sleeps. The electromagnetic radiation provided to eyelids 28 and 30 may be at wavelengths that are absorbed by the photoluminescent materials forming radiation source 64. The provision of electromagnetic radiation to the eyelids 28 and 30 may be controlled such that the electromagnetic radiation generated by radiation source 64 upon receiving electromagnetic radiation that has passed through upper eyelid 28 and lower eyelid 30 will be delivered to eyeball 26 in accordance with a light therapy algorithm. For instance, the device may provide at least some of the functionality attributed to illumination module 14, power module 16, and/or processor 18 described above with respect to FIG. 1. By way of non-limiting example, the device may include the sleep mask with one or more radiation sources integrated therein described in U.S. Provisional Patent Application 61/141,289, incorporated by reference above.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of providing light therapy to a subject, the method comprising:
   generating visible light between an eyeball and an eyelid of the subject; and
   delivering the visible light to an eyeball of a subject under the eyelid of the subject while the subject is asleep to impact melatonin and/or serotonin levels according to a light therapy algorithm, wherein delivering visible light to the eyeball of the subject under the eyelid of the subject while the subject is asleep comprises converting the wavelength of visible light that has passed through the eyelid of the subject to a therapeutically beneficial wavelength and delivering the visible light having the therapeutically beneficial wavelength to the eyeball of the subject,
   wherein delivering the visible light to the eyeball of the subject comprises generating visible light with one or more radiation sources carried by a radiation introduction module installed under the eyelid between the eyelid and the eyeball.

2. The method of claim 1, wherein generating the visible light between the eyeball and the eyelid of the subject comprises generating the visible light with the one or more radiation sources carried by the radiation introduction module installed under the eyelid between the eyelid and the eyeball.

3. The method of claim 1, wherein the visible light delivered to the eyeball has a therapeutically beneficial wavelength between 410 nm and 580 nm.

4. The method of claim 1, wherein delivering visible light to the eyeball of the subject under the eyelid of the subject while the subject is asleep is performed at least in part by a lens that sits on the eyeball of the subject, and wherein the lens is configured to selectively block visible light within a predetermined range of wavelengths from reaching the eyeball of the subject if the eyelid of the subject is open.

5. The method of claim 1, wherein delivering visible light according to a light therapy algorithm includes controlling one or more of an intensity, a flux, a timing, a duration, a pulse frequency, a pulse width, an illumination direction, an illumination pattern, or a subtended angle of illumination of the electromagnetic radiation.

6. A system configured to provide light therapy to a subject, the system comprising:
   a radiation introduction module configured to rest under an eyelid between an eyeball and the eyelid of a subject during use, wherein the radiation introduction module is configured to, while under the eyelid, generate visible light between the eyeball and the eyelid of the subject and deliver the visible light to the eyeball of the subject under the eyelid of the subject while the subject is asleep to provide light therapy to the subject, wherein the radiation introduction module is configured to receive visible light that has passed through the eyelid of the subject, to convert the wavelength of the received visible light to a therapeutically beneficial wavelength, and to deliver the visible light having the therapeutically beneficial wavelength to the eyeball of the subject; and
   a processor configured to control introduction of the visible light to the eyeball of the subject to impact melatonin and/or serotonin levels according to a light therapy algorithm, wherein controlling the introduction of the visible light according to the light therapy algorithm includes controlling an intensity of the visible light, and
   wherein controlling the intensity comprises ramping an illuminance of the visible light in accordance with a sigmoid intensity progression.

7. The method of claim 5, wherein delivering visible light according to the light therapy algorithm includes controlling the intensity, and wherein controlling the intensity comprises ramping an illuminance of the visible light in accordance with a sigmoid intensity progression.

8. The system of claim 6, further comprising one or more radiation sources carried by the radiation introduction module between the eyeball and the eyelid of the subject if the radiation introduction module is installed in the eye of the subject and the subject is asleep, and wherein the one or more radiation sources are powered to emit the visible light delivered to the eyeball of the subject by the radiation introduction module.

9. The system of claim 6, wherein the visible light delivered to the eyeball has a therapeutically beneficial wavelength between 410 nm and 580 nm.

10. The system of claim 6, wherein the radiation introduction module comprises a lens that sits on the eyeball of the subject, and wherein the lens is configured to selectively block visible light within a predetermined range of wavelengths from reaching the eyeball of the subject if the eyelid of the subject is open.

* * * * *